United States Patent [19]

Damlin et al.

[11] Patent Number: 4,971,441
[45] Date of Patent: Nov. 20, 1990

[54] METHOD AND APPARATUS FOR DETERMINING THE CONCENTRATION OF A SUBSTANCE WHICH IS BONDED TO PARTICLES IN A FLOWING MEDIUM

[75] Inventors: Sven-Arne Damlin, Bengtfors; Lars-Erik Falt, Amal; Sevin Valheim, Saffle, all of Sweden

[73] Assignee: BTG Kalle Inventing AB, Sweden

[21] Appl. No.: 314,899

[22] Filed: Feb. 24, 1989

[30] Foreign Application Priority Data

Feb. 26, 1988 [SE] Sweden .............................. 8800686

[51] Int. Cl.⁵ ............................................ G01N 21/53
[52] U.S. Cl. .................................... 356/338; 356/246
[58] Field of Search ....................... 356/336, 338, 246

[56] References Cited

U.S. PATENT DOCUMENTS 4,078,863  3/1978  Eriksson et al. ................ 356/336 X Primary Examiner—Davis L. Willis
Assistant Examiner—Matthew W. Koren
Attorney, Agent, or Firm—Ostrolenk, Faber, Gerb & Soffen

[57] ABSTRACT

The invention relates to a method and apparatus for determining the concentration of a substance which is bonded to particles in a flowing medium, where said substance can be present in varying concentrations, a light beam ($I_0$) being transmitted in the medium and light ($I_r$) directly reflected from the particles being detected for obtaining a signal which is proportional to the intensity of the reflected light, said signal being used as a measure of the concentration of the substance conditional on particle concentration and opticle properties of the particles being kept constant. Detection is carried out without light passing straight through the medium, by the particle concentration of the sample taken being selected sufficiently great so that the quantity of directly reflected light will be maximum. Apart from a first detector (1) for transmitting a light beam and for detecting light directly reflected from the particles for obtaining a first signal, the apparatus includes a second transducer (12) adapted to provide a signal (C) which is combinable with the first signal ($I_r$) and which represents the concentration and optical properties of the particles.

6 Claims, 3 Drawing Sheets

METHOD AND APPARATUS FOR DETERMINING THE CONCENTRATION OF A SUBSTANCE WHICH IS BONDED TO PARTICLES IN A FLOWING MEDIUM

The present invention relates to a method and an apparatus for determining the concentration of a substance which is bonded to particles in a flowing medium, where said substance can be such as lignin in paper pulp.

In the production of cellulose fibers for the manufacture of paper, board, cardboard etc, the fiber stock, e.g. wood chips, is treated with chemicals at raised pressure and temperature, so that parts of the material are liberated. The fibers in the material can then be uncovered with the aid of mechanical processing. The lignin content is in this case the subject of interest for measurement.

Delignification starts in the fiber wall. Not until this has been in progress some time does the delignification in the central lamella take place and subsequently continue throughout the whole of the wood structure. At the termination of the liberation, the lignin content in the single fibers is thus substantially greater at the periphery of the fiber than at its core. As in all chemical reactions, the temperature also has an effect on the delignification rate, which can be expressed by Arrhenius equation.

For obtaining a measure of the delignification for different combinations of time and temperature the so-called H factor has been introduced. For all other variables, except when time and temperature are constant, the H factor is a direct measure of the lignin content or the so-called Kappa number.

The primary object in pulp production is therefore to minimize the variations in the Kappa number. This is usually measured chemically by measuring potassium permanganate consumption in the oxidization of a given quantity of pulp. The measurement takes place manually and is both costly and time-consuming.

To facilitate this measurement a number of attempts have been made to provide an instrument which can continuously measure the lignin content. O'Meara in the U.S.A. has based his method on a plurality of samples that have been taken out and washed and collected in a reactor for reaction with nitric acid under pressure for a given time. The liquid is then colored yellow in inverse proportion to the degree of delignification and the color shade is measured photometrically.

Another method is based on the use of a fiber cake which is pressed under mechanical pressure and is dried to a constant dry content. The temperature rise during blowing through the cake with chlorine gas then consists of a measure of the lignin content, since the reaction between chlorine and lignin is exothermic.

The disadvantages of the mentioned methods are that they consume chemicals in the measurements, something which is not desirable in continuous measurements. The latter method has also been found to give rise to large corrosion problems, since chlorine gas is strongly aggressive to most materials.

Other apparatuses are envisaged as pure automation of laboratory determination methods such as Kappa number measurement in potassium permanganate titration.

It has been known since the forties that the light absorption of lignin has a maximum in the UV range. Attempts have been made several times to utilize this principle for determining the lignin content. On the majority of occasions measurements have only been made on black liquor. These have not resulted in any commercial instruments.

A commercial instrument for optically determining lignin content does exist, however. In this case a pulp suspension is allowed to flow through a measuring cell and a detector determines the radiation passing through the flowing medium, another detector being used to measure the radiation which the fibers spread in a given direction. The suspension must be diluted so that there is very small probability that the light will be reflected against more fibers before it arrives at one of the detectors.

The object of the present invention is to provide a method and an apparatus for determining the concentration of a substance, e.g. lignin which is bonded to particles, e.g. cellulose fibers in a flowing medium, the disadvantages in methods and apparatuses used so far being entirely eliminated. With the aid of the apparatus in accordance with the invention there has been eliminated the previously used measuring cell, which is very sensitive to air bubbles while requiring at the same time measurement in a concentration range of 0.02–0.03%, i.e. the use of very large volumes, whereas the inventive apparatus can measure in a concentration range of 0.2–0.3%, for example, resulting in that a sample volume 10 times as small can be used, which makes sample taking substantially more simple simultaneously as the apparatus required for measurement can be made less voluminous.

BRIEF DESCRIPTION OF THE DRAWINGS

The invention will now be described in more detail with the aid of a preferred embodiment and with reference to the accompanying drawings, where.

DETAILED DESCRIPTION OF THE PREFERRED EMBODIMENTS

Figure 1:
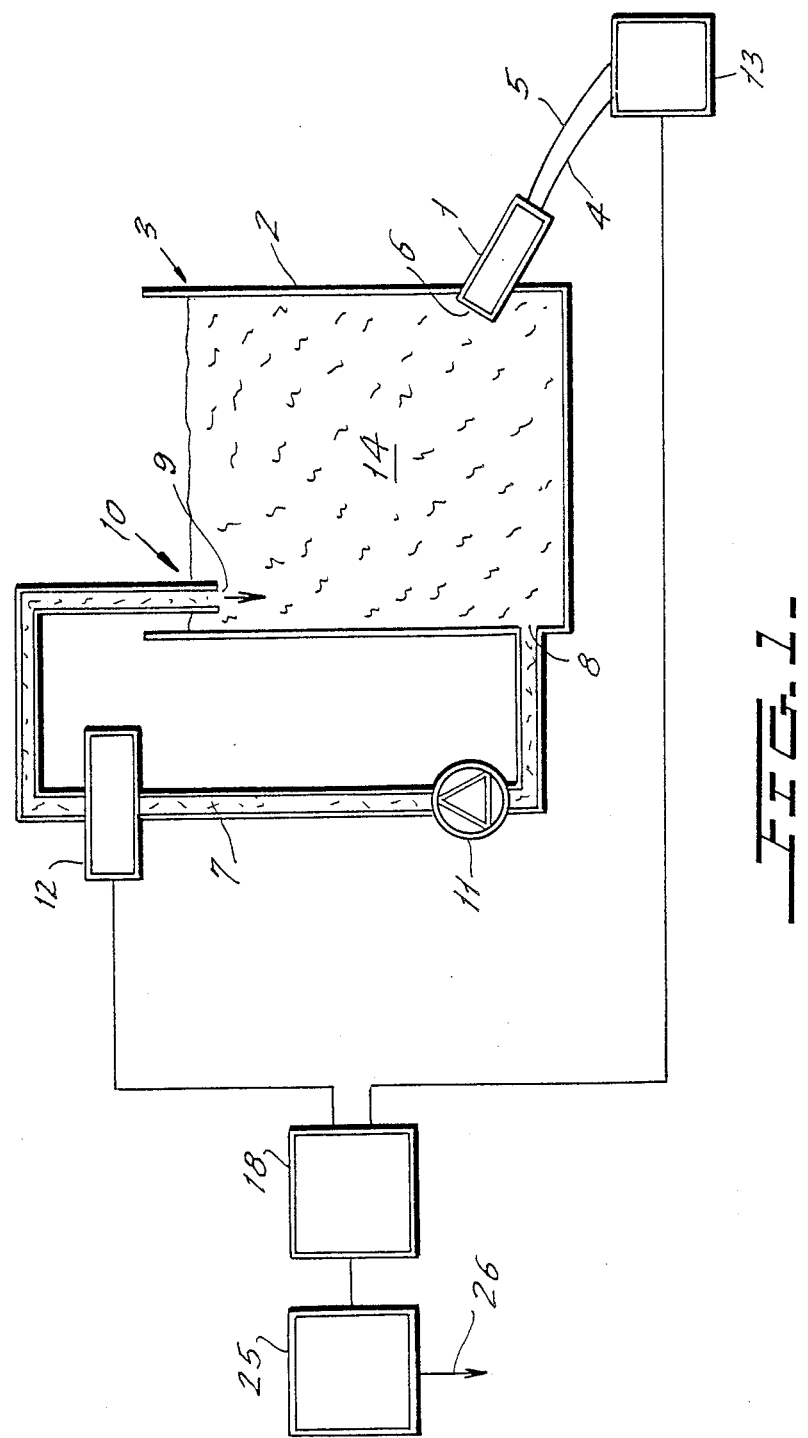
FIG. 1 is a schematic application of the apparatus in accordance with the present invention.
Figure 2:
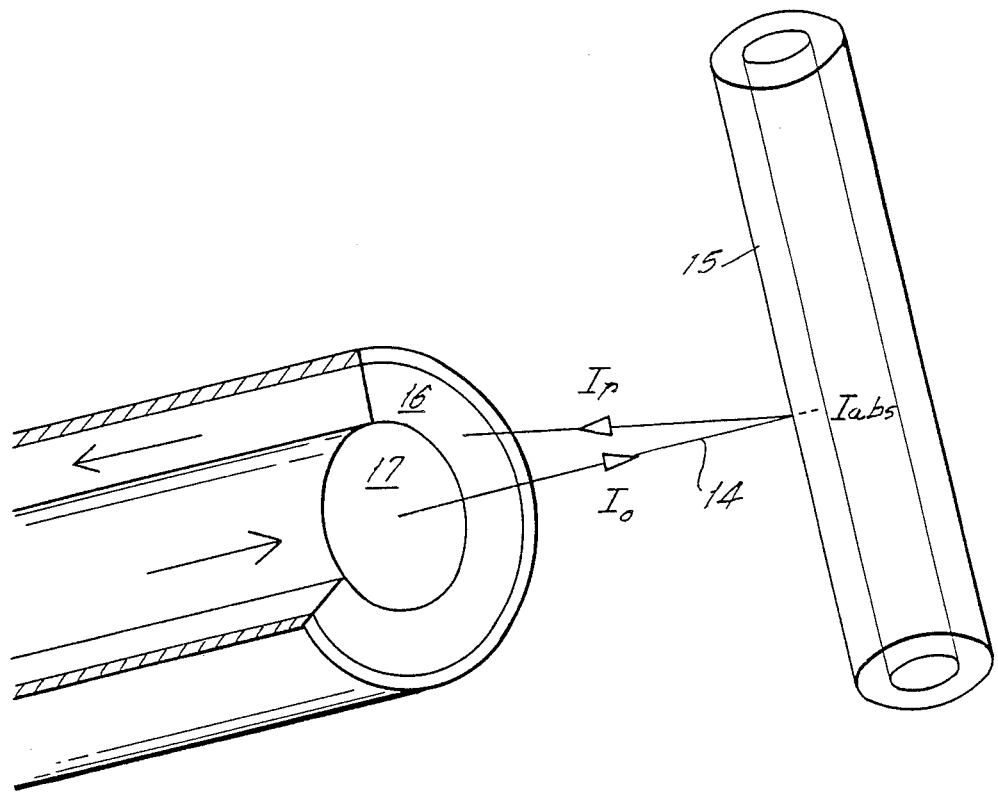
FIG. 2 is a schematic perspective view of how a light flow from an insertion probe in the apparatus according to FIG. 1 is reflected against a cellulose fiber, and FIG. 3 schematically illustrates in cross section a depolarisation detector included in the apparatus illustrated in FIG. 1.
Figure 3:
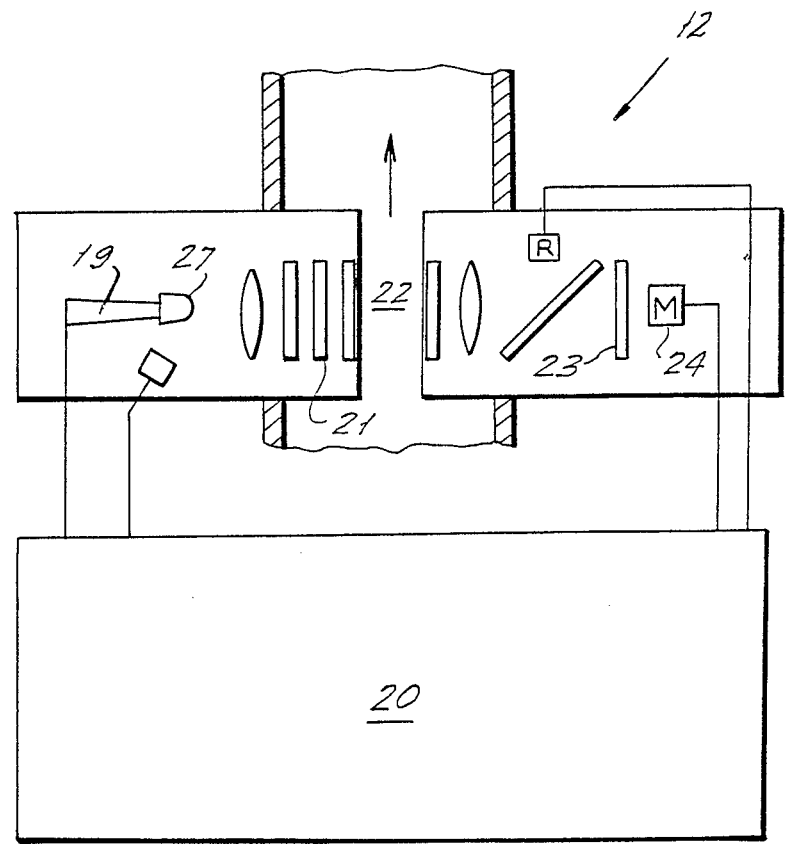

The apparatus according to a preferred embodiment of the present invention comprises a first transducer 1, formed as an insertion probe, which is mounted in the wall 2 of a sample container The transducer 1 includes two light conductors 4, 5 extending into and terminating in the end wall 6 of the transducer. A pump line 7 is taken from an opening 8 at the bottom of the sample container 3 and extends such that it has its other end opening 9 at the upper part 10 of the sample container 3. The sample volume which has been led into the sample container 3 can be caused to circulate via this line 7 with the aid of a pump 11 included in the line. A second transducer 12, implemented as a depolarisation detector, is mounted in the pump line 7. Since the insertion probe or the first transducer 1 is adapted to measure directly reflected light sent from an optical unit 13 and which has been reflected against the suspended particles, a particle concentration range, e.g. of 0.2–0.3%, can be measured. The transducer 1 is suitably mounted at an angle in the wall 2 to avoid reflection on the opposing wall 2 of the sample container 3. In determination of concentration, light $I_0$ from the light conductors 4,5 of the transducer 1 are sent into a medium, e.g. a pulp suspension 14, which flows with high turbulence towards the end wall 6 of the transducer 1. The light $I_r$ which is reflected from the fibers 15 of the suspension 14 and received by a light conductor part 16 in the transducer 1 placed concentrically about a light conductor part 17 for the transmitted light $I_0$ is filtered to a predetermined wavelength (e.g. 280 nm for lignin, although this depends on what substance it is desired to measure) before it arrives at a detector in the optical unit 13. The signals from the depolarisation detector or transducer 12 and the optical unit 13 then go to signal adaptation electronics 18, where they are processed and sent to a calculating unit 25 which supplies an output signal 26 indicating the Kappa number of the sample.

It has been mentioned above that lignin has a maximum absorption at a special wavelength in the UV range. The light strength arriving at the detector is thus a measure of the lignin content in the fiber 15. The more light arriving at the detector the less has been absorbed in the fiber 15, which indicates a low lignin content and thereby a low Kappa number.

Since the measurement is done in the UV range, there are no chromophoric groups giving rise to disturbances, and there is thus no effect from color changes. As long as the same type of fiber is measured, there is thus obtained good correlation between Kappa numbers determined by using detected light strength and Kappa numbers determined chemically in permanganate titrations in the method mentioned above.

However, it is a known phenomenon that in optical transducers the light reflection is heavily dependent on the specific surface of the fibers. A large specific surface gives rise to greater reflection than a small specific surface. The light strength that the detector in the optical unit 13 receives is thus the result of a combination of lignin content and specific surface. The process can be expressed mathematically according to the following:

$$I_r = (I_0 - I_{abs})(1-r)$$

where $I_r$ is the reflected light quantity, $I_0$ the light quantity transmitted in the suspension and $I_{abs}$ is the light quantity absorbed in the lignin. $I_{abs}$ thus increases with increasing lignin concentration. A constant r is determined by the kind of wood and/or fiber length distribution. To compensate for this, the transducer or depolarisation detector 12 is used in accordance with the present invention, this detector including a measuring cell 19 with an electronic unit 20 for measuring the depolarising effect of the fiber suspension. Light transmitted from a light source 27 is polarised in a polarisation filter 21 in the measuring cell 19 and passes a measuring slit 22, through which the fiber suspension 14 flows, to continue through a second polarisation filter 23 turned 90° in relation to the first one, before this light reaches a detector 24, which gives a signal.

Variations in this signal are an expression of the depolarising effect of the fiber 15. It is known that the depolarising effect is proportional to the concentration of the pulp suspension, and furthermore that it depends on fiber type and/or fiber length distribution. The latter is explained by the detector 12 not only being sensitive to depolarisation but also to the degree of turning of the polarisation vector of the incident light. This is due to cellulose being optically active. The signal from the detector or transducer 12, hereinafter denoted C, is a measure of the combination of pulp concentration and kind of wood and/or fiber length distribution. Together, these signals $I_r$ and C will agree well with the lignin content measured chemically.

For on-line measurement, a sample is taken from a pulp line, and is first subjected to a washing and/or screening sequence, subsequent to which a measuring sequence is started. The mean values of the measurements are denoted $I_{r1}$ and $C_1$. The suspension is diluted with water to obtain a lower concentration. After a further procedure according to the above, the signals $I_{r2}$ and $C_2$ are obtained. The signals for $I_{r1,2}$ and $C_{1,2}$ are assumed to be linear in the interval in question. Values corresponding to $I_{r1,2}$ and $C_{1,2}$ were measured in pure water and denoted $I_{r0}$ and $C_0$ are subtracted from the values $I_{r1,2}$ and $C_{1,2}$ to obtain $$I'_{r1,2} = I_{r1,2} - I_{r0} \text{ and } C'_{1,2} = C_{1,2} - C_0$$

or $$I'_{r1} = I_{r1} - I_{r0}; C'_1 = C_1 - C_0$$

$$I'_{r2} = I_{r2} - I_{r0}; C'_2 = C_2 - C_0$$

The directional coefficient and intersection point for the straight line between $(I'_{r1}, C'_1)$ and $(I'_{r2}, C'_2)$ is calculated.

The directional coefficient and intersection point for this line are respectively denoted a and b hereinafter. These have been found to be characteristic for each individual fiber type in different combinations of lignin content and fiber length distribution. Accordingly, this means that there is no dependence on knowing the actual concentration. All that it is necessary to do is to measure the signals at two different concentration levels. In measuring several calibration suspensions, the coefficients $K_0$, $K_1$, $K_2$ and $K_3$ are obtained, which are included in the equation for calculating the Kappa number, $\kappa$.

$$\kappa = K_0 + K_1 \cdot a + K_2 \cdot b + K_3 \cdot a \cdot b$$

where $K_0$, $K_1$, $K_2$, $K_3$ are constants, a is the directional coefficient and b the intersection point for the straight line between $(I'_{51}, C'_1)$ and $(I'_{r2}, C'_2)$.

We claim:

1. A method of measuring the concentration of a substance which is bonded to particles in a flowing medium, the method comprising the steps of:
   transmitting light $I_0$ into the flowing medium such that light $I_r$ is reflected by the particles, the concentration of the particles being sufficiently great such that the transmitted light $I_0$ does not pass entirely through the medium;
   detecting the intensity of the reflected light $I_r$; and
   determining the concentration of the substance as a function of the intensity of the reflected light $I_r$.

2. The method of claim 1, wherein the medium is a sample from a pulp line, the substance being lignin.

3. A method of measuring the concentration of a substance which is bonded to particles in a flowing medium to be measured, the method comprising the steps of:
   transmitting light $I_0$ into the flowing medium such that light $I_r$ is reflected by the particles, the concentration of the particles being sufficiently great such that the transmitted light $I_0$ does not pass entirely through the medium;

detecting the intensity of the reflected light $I_r$ and obtaining a first signal which is representative of the intensity of the reflected light $I_r$;

obtaining a second signal which is representative of the concentration of the particles and the optical properties of the particles; and determining the concentration of the substance as a function of the first and second signals.

4. The method of claim 3, wherein the second signal is obtained by a depolarization detector.

5. The method of claim 3, further comprising the steps of:

forming a diluted medium by diluting the medium to be measured;

transmitting light $I_0'$ into the diluted medium such that light $I_r'$ is reflected by the particles, the concentration great such that the transmitted light $I_0'$ does not pass entirely through the diluted medium;

detecting the intensity of the reflected light $I_r'$ and obtaining a third signal which is representative of the intensity of the reflected light $I_r'$; and obtaining a fourth signal which is representative of the concentration of the particles in the diluted medium and the optical properties of the particles;

wherein the step of determining the concentration of the substance includes determining the concentration of the substance as a function of the first, second, third and fourth signals.

6. An apparatus for measuring the concentration of a substance which is bonded to particles in a flowing medium, the apparatus comprising:

a first transducer for transmitting light $I_0$ such that light $I_r$ is directly reflected by the particles, for detecting the directly reflected light $I_r$ and for obtaining a first signal which is proportional to the intensity of the directly reflected light $I_r$;

a second transducer for obtaining a second signal which is representative of the concentration of the particles and the optical properties of the particles; and means for using the first and second signals to determine the concentration of the substance in the flowing medium.

* * * * *